United States Patent [19]
Hori et al.

[11] Patent Number: 6,146,656
[45] Date of Patent: *Nov. 14, 2000

[54] PERCUTANEOUS ABSORPTION PREPARATION

[75] Inventors: Mitsuhiko Hori; Kenjiro Minomi; Yoshihisa Nakano, all of Osaka, Japan

[73] Assignee: Nitto Denko Corporation, Osaka, Japan

[*] Notice: This patent issued on a continued prosecution application filed under 37 CFR 1.53(d), and is subject to the twenty year patent term provisions of 35 U.S.C. 154(a)(2).

[21] Appl. No.: 09/232,684

[22] Filed: Jan. 19, 1999

[30] Foreign Application Priority Data

Jan. 22, 1998 [JP] Japan .................. 10-010034
Jan. 23, 1998 [JP] Japan .................. 10-011023

[51] Int. Cl.$^7$ .......................... A61F 13/02; A61K 31/445
[52] U.S. Cl. .......................... 424/448; 514/319
[58] Field of Search ................... 424/448, 449, 424/484; 514/772, 319; 528/364; 524/394

[56] References Cited

U.S. PATENT DOCUMENTS

| | | | |
|---|---|---|---|
| 4,863,738 | 9/1989 | Taskovich | 424/449 |
| 5,120,546 | 6/1992 | Hansen et al. | 424/449 |
| 5,176,916 | 1/1993 | Yamanaka et al. | 424/448 |
| 5,328,696 | 7/1994 | Noel | 424/449 |
| 5,556,636 | 9/1996 | Yano et al. | 424/448 |
| 5,607,691 | 3/1997 | Hale et al. | 424/449 |
| 5,656,286 | 8/1997 | Miranda et al. | 424/449 |
| 5,719,197 | 2/1998 | Kanios et al. | 514/772.6 |
| 5,851,549 | 12/1998 | Svec | 424/448 |
| 5,869,598 | 2/1999 | Yoshida et al. | 528/364 |
| 5,877,173 | 3/1999 | Olney et al. | 514/217 |
| 6,024,976 | 2/2000 | Miranda et al. | 424/449 |

FOREIGN PATENT DOCUMENTS

| | | |
|---|---|---|
| 0 276 735 | 8/1988 | European Pat. Off. . |
| 0 380 989 | 8/1990 | European Pat. Off. . |
| 2 623 401 | 5/1989 | France . |
| 2 163 347 | 2/1986 | United Kingdom . |
| 9115176 | 10/1991 | WIPO .............. A61F 13/00 |
| WO 91/15176 | 10/1991 | WIPO . |
| WO 98/00141 | 1/1998 | WIPO . |

OTHER PUBLICATIONS

Tan U., Electrocorticographic changes induced . . . , Electroenfcephalography and Clinical Neurophysiology, v 42/2, p. 252–258, 1977.

*Primary Examiner*—William R. A. Jarvis
*Assistant Examiner*—Vickie Kim
*Attorney, Agent, or Firm*—McGuireWoods, LLP

[57] ABSTRACT

The present invention provides a percutaneous absorption preparation which comprises a skin contact base containing therein at least one active ingredient selected from the group consisting of biperiden, trihexyphenidyl and pharmacologically acceptable salts thereof in an amount of from 0.5 to 60% by weight. The percutaneous absorption preparation makes it possible to permit the percutaneous absorption of biperiden, trihexyphenidyl or pharmacologically acceptable salt thereof as an active ingredient so that the medicament can be used effectively and at the same time, pharmacological effects can be sustained long and administration can be carried out conveniently. In addition, the active ingredient contained in it can be maintained stably.

8 Claims, 1 Drawing Sheet

PERCUTANEOUS ABSORPTION PREPARATION

FIELD OF THE INVENTION

This invention relates to a percutaneous absorption preparation which comprises as an active ingredient at least one antiparkinsonism drug selected from biperiden, trihexyphenidyl or pharmacologically acceptable salts thereof, permits the percutaneous penetration of the active ingredient in the body, and has excellent stability.

BACKGROUND OF THE INVENTION

Biperiden and trihexyphenidyl are known as anticholinergic antiparkinsonism drugs and are used for the adjunctive treatment of all forms of parkinsonian syndrome. They are administered by injections or tablets. The medicament which is orally administered, for example, as tablets and absorbed in the body are inevitably subjected to decomposition in the digestive organs and primary metabolism in the liver. Accordingly, it is desired to adopt a percutaneous absorption method through the skin surface in consideration of the availability of the administered medicament, long-lasting pharmacological effects and convenience in administration.

With the above-described conventional technique in view, the present inventors have carried out an extensive investigation on the percutaneous absorption of biperiden, trihexyphenidyl or pharmacologically acceptable salt thereof such as biperiden hydrochloride or trihexyphenidyl hydrochloride. As a result, it has been found that a percutaneous absorption preparation which has excellent percutaneous absorption and is stable can be obtained by incorporating such an active ingredient in a skin contact base in an amount ranging from 0.5 to 60% by weight.

SUMMARY OF THE INVENTION

An object of the present invention is to provide a percutaneous absorption preparation, which comprises at least one active ingredient selected from the group consisting of biperiden, trihexyphenidyl and pharmacologically acceptable salts thereof in a skin contact base in an amount ranging from 0.5 to 60% by weight.

The percutaneous absorption preparation according to the present invention makes it possible to permit the percutaneous absorption of biperiden, trihexyphenidyl or pharmacologically acceptable salt thereof as an active ingredient so that the medicament can be used effectively and at the same time, pharmacological effects can be sustained long and administration can be carried out conveniently. In addition, the active ingredient contained in it can be maintained stably.

DETAILED DESCRIPTION OF THE INVENTION

Figure 1:
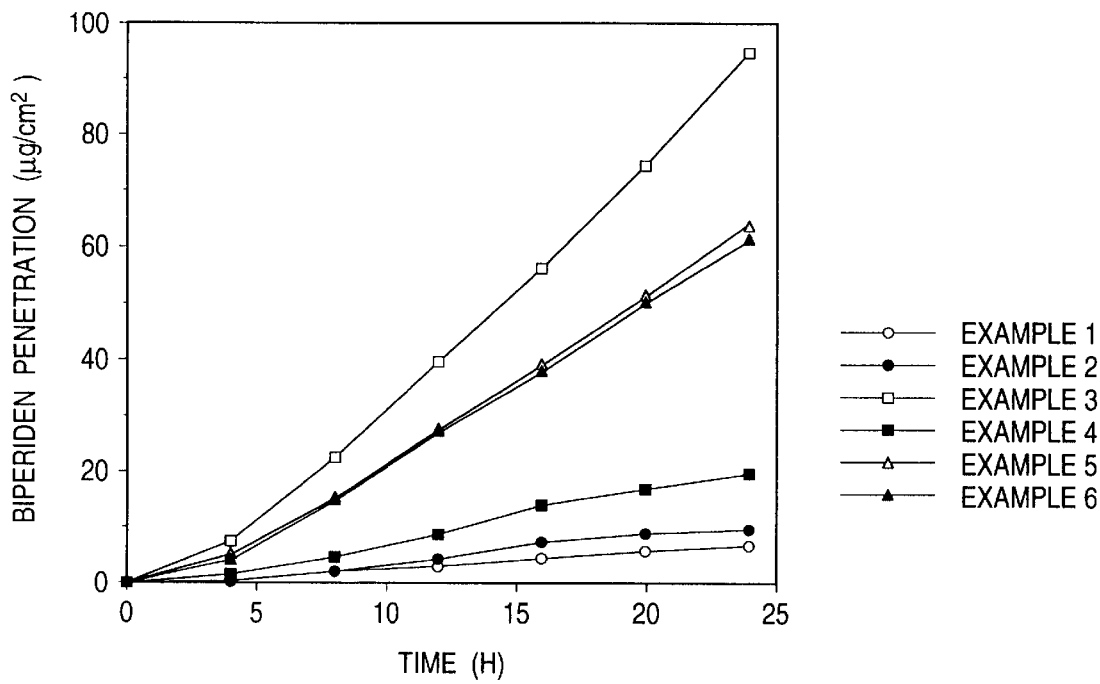
FIG. 1 is a graph illustrating the testing results of the preparations obtained in Examples 1 to 6.

Biperiden or trihexyphenidyl to be incorporated in the percutaneous absorption preparation of the present invention as an active ingredient is employed mainly for the treatment of the Parkinson disease, but is not limited to such purpose and it may exhibit another pharmacological action. Examples of the pharmacologically acceptable salt include hydrochloride, sulfate, succinate and lactate, of which the hydrochloride is preferred. In the percutaneous absorption preparation of the present invention, the pharmacologically acceptable salt may exist as a free form in the skin contact base. Described specifically, a pharmacologically acceptable salt of biperiden or trihexyphenidyl is changed to its free form, that is, biperiden or trihexyphenidyl in the skin contact base by allowing the salt to exist together with a freeing agent such as sodium hydroxide, potassium hydroxide, tetraethylamine, tetraethylammonium, ammonia or sodium caprylate. From the viewpoint of percutaneous absorption, the active ingredient to be incorporated in the skin contact base is preferred in the order of biperiden (or trihexyphenidyl), freed form of biperiden (or freed form of trihexyphenidyl) and pharmacologically acceptable salt of biperiden (or trihexyphenidyl). But, the above-described order is not always true from the viewpoint of stability with the passage of time. It is recommended to select the active ingredient in consideration of the balance between the percutaneous absorption and stability with time.

In the percutaneous absorption preparation of the present invention, it is possible to incorporate at least one active ingredient selected from the group consisting of biperiden, trihexyphenidyl and pharmacologically acceptable salt thereof in an amount of 0.5 to 60% by weight, preferably 1 to 30% by weight. When the content is less than 0.5% by weight, it is difficult to permit the absorption of the medicament in an amount sufficient for exhibition of its pharmacological effects. The contents exceeding 60% by weight, on the other hand, lower the skin adhesion, thereby making it difficult to surely adhere the medicament to the skin surface.

There is no particular limitation imposed on the skin contact base in which the above-described active ingredient is to be incorporated, insofar as it is brought into contact with the skin and permits percutaneous administration of the above active ingredient from the skin surface. Specific examples of the base include those constituting a semi-solid or solid preparation such as ointment, gel, emulsion, suspension, cataplasm or plaster or a liquid preparation such as lotion or liniment.

As the ointment base, hydrophobic bases such as oils and fats, waxes and hydrocarbons can be employed usually. Specific examples include mineral bases such as yellow vaseline, white vaseline, paraffin, liquid paraffin, plastibase and silicone and animal or vegetable bases such as beeswax and animal or vegetable oils and fats.

For the gel preparation, hydrogel base such as carboxyvinyl polymer, gel base, fat-free ointment and polyethylene glycol can be used.

Examples of the base for emulsion include water-in-oil type bases such as hydrophilic ointment and vanishing cream, and oil-in-water type bases such as hydrophilic vaseline, purified lanolin, aquahole, oicerin, neocerin, hydrogenated lanolin, cold cream and hydrophilic plastibase.

Examples of the base for suspension include lotion and FAPG base (fatty alcohol-propylene glycol) having fine particles such as stearyl alcohol or cetyl alcohol suspended in propylene glycol, that is, a lyogel base.

Examples of the base for cataplasm include gelatin, carboxymethyl cellulose sodium, methyl cellulose, sodium polyacrylate, kaolin, polyvinyl alcohol, polyvinyl pyrrolidone, glycerin, propylene glycol and water.

A lotion is a preparation having an active ingredient finely and uniformly dispersed in an aqueous liquid and can be classified into suspending lotion and emulsion lotion. Examples of the suspending agent include gum arabic, sodium alginate, carboxymethyl cellulose sodium, methyl cellulose and bentonite. Examples of the emulsifying agent include sodium laurylsulfate, Tweens and Spans.

Liniment can be classified into oily solution type, alcohol solution type, emulsion type and suspension type. To such a liniment, an additive such as water, ethanol, fatty oil, glycerin, soap, emulsifying agent or suspending agent may be added. A base usable for a plaster in the percutaneous absorption preparation of the present invention will be described later.

The preparation of the present invention can be prepared by a known method. For example, the above-described ointment can be prepared by the ordinary mixing or fusion method. In the mixing method, the preparation is obtained by mixing the active ingredient with a portion of a base, adding the remaining portion to the resulting mixture and mixing them to homogenize the mixture. For mass production, a kneader, roll mill or mixer is employed. In the fusion method, base components are molten in the descending order of a melting component and they are mixed until solidified. For mass production, a mixer or three-roll mill is employed. The dermatologic paste or cataplasm resembles to the ointment, but the dermatologic paste contains a comparatively large amount of the active ingredient powder compared with the ointment. The paste is prepared in accordance with the method used for the ointment, but in general, the fusing method is employed. The cataplasm is an external preparation used as a poultice and it contains the active ingredient powder and essential oil ingredient.

In the percutaneous absorption preparation of the present invention, it is preferred to employ a plaster in the form of a pressure-sensitive adhesive tape in which a so-called pressure-sensitive adhesive which has adhesion at normal temperature is used as a skin contact base in consideration of the handling ease, adhesion to the skin and improvement of percutaneous absorption when used in occlusive dressing technique and a layer of the pressure-sensitive adhesive is formed on one side of a backing material from the viewpoint of the handling ease.

The above-described pressure-sensitive adhesive layer is preferably formed of an ordinarily-employed medical pressure-sensitive adhesive with a view to preventing rashes caused by the contact of the adhesive layer with the surface of the skin. Examples thereof include acrylic pressure-sensitive adhesives; natural rubber pressure-sensitive adhesives; synthetic rubber pressure-sensitive adhesives such as synthetic isoprene rubber, polyisobutylene rubber, styrene/butadiene rubber, styrene/isoprene/styrene rubber and styrene/butadiene/styrene rubber; silicone pressure-sensitive adhesives; vinyl ester pressure-sensitive adhesives; and vinyl ether pressure-sensitive adhesives. It is preferred to use, among them, at least one adhesive selected from acrylic, rubber or silicone pressure-sensitive adhesive in consideration of stable quality and easy adjustment of adhesion properties. Particularly, acrylic pressure-sensitive adhesives comprising alkyl acrylate or alkyl methacrylate as the main component are preferred.

As the above-described acrylic pressure-sensitive adhesive, polymers prepared by polymerizing an alkyl (meth)acrylate in a proportion not less than 40% by weight based on the total amount of the monomers to be polymerized are preferred. Copolymers prepared by copolymerizing 50 to 98% by weight of one or more alkyl (meth)acrylates and 2 to 50% by weight of one or more copolymerizable monomers are particularly preferred.

Examples of such an alkyl (meth)acrylate include esters of from a primary to tertiary alcohol having a $C_{2-18}$, preferably $C_{4-12}$, alkyl group and acrylic or methacrylic acid.

Examples of the copolymerizable monomer include monomers each having in its molecule at least one unsaturated double bond which takes part in the copolymerization reaction and in its side chain a functional group such as carboxyl group (for example, (meth)acrylic acid, itaconic acid, maleic acid or maleic anhydride), hydroxyl group (for example, hydroxyethyl (meth)acrylate or hydroxypropyl (meth)acrylate), sulfoxyl group (for example, styrenesulfonic acid, allylsulfonic acid, sulfopropyl (meth)acrylate, (meth)acryloyloxynaphthalenesulfonic acid or acrylamidomethylpropanesulfonic acid), amino group (for example, aminoethyl (meth)acrylate, dimethylaminoethyl (meth)acrylate or tert-butylaminoethyl (meth)acrylate), amide group (for example, (meth)acrylamide, dimethyl (meth)acrylamide, N-butyl acrylamide, N-methylol (meth)acrylamide or N-methylolpropane (meth)acrylamide), or alkoxyl group (for example, methoxyethyl (meth)acrylate, ethoxyethyl (meth)acrylate, methoxyethyleneglycol (meth)acrylate, methoxydiethyleneglycol (meth)acrylate, methoxypolyethyleneglycol (meth)acrylate, methoxypolyethyleneglycol (meth)acrylate or tetrahydrofulfuryl (meth)acrylate).

Examples of the copolymerizable monomer include (meth)acrylonitrile, vinyl acetate, vinyl propionate, N-vinyl-2-pyrrolidone, methyl vinyl pyrrolidone, vinylpyridine, vinyl piperidone, vinyl pyrimidine, vinyl piperazine, vinyl pyrazine, vinyl pyrrole, vinyl imidazole, vinyl caprolactam, vinyl oxazole and vinyl morpholine.

The above-exemplified copolymerizable monomers can be provided for copolymerization either singly or in combination. From the viewpoints of adhesion properties such as adhesion or cohesion or releasability of biperiden, trihexyphenidyl or pharmacologically acceptable salt thereof from the pressure-sensitive adhesive layer, however, it is preferred to carry out copolymerization by using, as an essential ingredient, at least one monomer selected from a carboxyl-containing monomer and a hydroxyl-containing monomer in an amount of 1 to 50% by weight, preferably 3 to 20% by weight and, if necessary, the other monomer exemplifed above, for example, a vinyl monomer such as vinyl acetate or N-vinyl-2-pyrrolidone in an amount not greater than 40% by weight, preferably not greater than 30% by weight, each based on the total amount of the monomers to be polymerized.

Specific examples of the acrylic pressure-sensitive adhesive include copolymers of 2-ethylhexyl acrylate and acrylic acid, those of 2-ethylhexylacrylate and hydroxyethyl acrylate, those of 2-ethylhexylacrylate and methyl methacrylate, those of 2-ethylhexylacrylate, 2-methoxyethyl acrylate and vinyl acetate, those of 2-ethylhexyl acrylate and vinyl pyrrolidone, those of 2-ethylhexyl acrylate, methyl methacrylate and 2-methoxyethyl acrylate and those of 2-ethylhexyl acrylate, vinyl pyrrolidone and acrylic acid.

The acrylic pressure-sensitive adhesive which can be used in the present invention generally has a number-average molecular weight of from 10,000 to 100,000 and a weight-average molecular weight of from 100,000 to 2,000,000.

In the percutaneous absorption preparation of the present invention, it is possible to incorporate in the skin contact base at least one organic liquid ingredient selected from the group consisting of glycols, oils and fats, fatty acids, alcohols and fatty acid esters. Such an ingredient is able to bring about advantages such as improvement in skin adhesion or skin penetration of the active ingredient or lowering of the skin irritation.

Examples of the glycol include ethylene glycol, diethylene glycol, triethylene glycol, polyethylene glycol, propylene glycol and polypropylene glycol. As polyethylene glycol or polypropylene glycol having a high molecular weight, that having a weight average molecular weight of 200 to 1000 is preferably employed.

Examples of the oil and fat include olive oil, castor oil, squalane, orange oil and mineral oil.

Examples of the fatty acid include $C_{6-20}$ fatty acids such as monocapric acid, oleic acid, caprylic acid, lauric acid, undecylenic acid, isostearic acid and linoleic acid.

Examples of the fatty acid ester include $C_{6-20}$ fatty acid esters such as isopropyl myristate, diethyl sebacate, octyl palmitate, ethyl oleate, diethyl phthalate, diisopropyl adipate, ethyl lactate, propylene glycol fatty acid esters, lauryl nicotinate and laurylpyrrolidone carboxylate.

Examples of the alcohol include $C_{1-20}$ alcohols other than the above-described glycols, such as ethanol, methanol, octyl alcohol, ethoxylated stearyl alcohol, 1,3-butanediol, decyl alcohol, cineol and oleyl alcohol.

It is preferred that the organic liquid ingredient is incorporated in the skin contact base in an amount of from 2 to 50% by weight.

When the preparation of the present invention is used in the form of a plaster having a pressure-sensitive adhesive as the skin contact base, it is possible to improve the percutaneous penetration of the active ingredient by incorporating one or more of the above-described organic liquid components in the pressure-sensitive adhesive layer. The pressure-sensitive adhesive layer can be plasticized owing to its compatibility with the organic liquid ingredient so that the addition of such an organic liquid ingredient makes it possible to impart the skin with soft feeling upon adhesion to the skin surface. Furthermore, an appropriate cohesive force can be imparted to the pressure-sensitive adhesive layer by crosslinking treatment, whereby the skin irritation when the plaster is peeled and removed after use can be reduced.

The organic liquid ingredient is added to the pressure-sensitive adhesive layer in an amount of 25 to 200 parts by weight, preferably 40 to 180 parts by weight, particularly preferably 60 to 180 parts by weight per 100 parts by weight of the pressure-sensitive adhesive. Too small amount of the organic liquid ingredient does not bring about any advantages. Too large amount, on the other hand, lowers the cohesive force owing to excessive plasticization of the pressure-sensitive adhesive layer, which causes an adhesive residue phenomenon on the skin surface even after the cross-linking treatment, resulting in an increase in the skin irritation upon peeling.

In the present invention, it is possible to add, to the pressure-sensitive adhesive layer, rosin, a rosin derivative, a polyterpene resin, a chroman-indene resin, a petroleum resin or a terpene phenol resin as needed.

The above-described plaster requires a backing material for supporting the pressure-sensitive adhesive layer thereon. Examples of such a backing material include a single film or laminate film of cellulose acetate, ethyl cellulose, polyethylene terephthalate, polyethylene, polypropylene, vinyl acetate-vinyl chloride copolymer, soft polyvinyl chloride, polyurethane, polyvinylidene chloride, ethylene-vinyl acetate copolymer, Surlyn or polytetrafluoroethylene, various metallic foils and metal-deposited films. In addition, woven fabric or nonwoven fabric of fibers made of such a material, cloth and paper can also be employed.

As the backing material, sufficient flexibility and skin following property when the resulting percutaneous absorption preparation is applied to the skin surface can be used. The thickness of the backing material is generally from 0.5 to 200 µm, preferably from 2 to 100 µm, more preferably 5 to 50 µm.

With a view to improving the sustained releasability of the active ingredient, the percutaneous absorption preparation of the present invention can be-formulated as a sustained-release preparation by using a sustained-release base. Such a preparation can be obtained by incorporating a composition prepared by the ordinary means in a special matrix or can be obtained as a sustained-action preparation in which the composition is adhered to the skin surface through a film such that the release of the active ingredient is controlled by the film. As a film for such a sustained-release percutaneous absorption preparation, a microporous film having an average pore size of 0.1 to 1 µm can be employed. Examples of the material of the microporous film include polypropylene, polyolefin and polytetrafluoroethylene.

A plaster, which is one embodiment of the percutaneous absorption preparation of the present invention, can be obtained by adhering a release paper on one side of the pressure-sensitive adhesive layer and a backing layer on the other side. The pressure-sensitive adhesive layer is formed by dissolving the components of the pressure-sensitive adhesive in an appropriate solvent, applying the resulting solution to a backing material or peeling paper and then drying the resulting material or paper to remove the solvent.

In the skin contact base layer, it is possible to incorporate an additive such as antioxidant, pigment, filler, percutaneous absorption enhancer, stabilizing agent, drug dissolution aid or drug dissolution suppressing agent as needed in an amount ranging from about 2 to 50 parts by weight per 100 parts by weight of the skin contact base.

The present invention will hereinafter be described more specifically by examples. It should however be borne in mind that the present invention is not limited to or by these examples and can be applied within an extent not departing from the technical concept of the present invention. Incidentally, all designations of "part" or parts" and "%" mean part or parts by weight and % by weight, respectively.

EXAMPLE 1

To an ethyl acetate solution of an acrylic pressure-sensitive adhesive [a 95:5 (weight ratio) copolymer of 2-ethylhexyl acrylate and acrylic acid], 10 parts of biperiden hydrochloride and 40 parts of isopropyl myristate, each relative to 50 parts of the solid content of the pressure-sensitive adhesive, were added, followed by the addition of 0.15 part, relative to 100 parts of the solid content of the pressure-sensitive adhesive, of an isocyanate crosslinking agent. The resulting mixture was mixed uniformly to obtain a plaster solution. The resulting plaster solution was applied to one side of a polyester film serving as a separator to give a dry thickness of 40 µm and dried, whereby a pressure-sensitive adhesive layer was formed.

The pressure-sensitive adhesive layer so formed was adhered to one side of an ethylene-vinyl acetate copolymer film (thickness: 25 µm) serving as a backing material, whereby a percutaneous absorption preparation of the present invention was obtained.

EXAMPLE 2

A pressure-sensitive adhesive layer was formed in the same manner as in Example 1 except that an ethyl acetate solution of an acrylic pressure-sensitive adhesive [a 75/3/22

(weight ratio) copolymer of 2-ethylhexyl acrylate, acrylic acid and vinyl pyrrolidone] was used and the isocyanate crosslinking agent was added in an amount of 0.4 part per 100 parts of the solid content of the pressure-sensitive adhesive.

The pressure-sensitive adhesive layer so formed was adhered to the surface of the nonwoven fabric side of a laminate made of a polyester film (thickness: 6 $\mu$m) and polyester nonwoven fabric (basis weight: 8 g/m$^2$), whereby a percutaneous absorption preparation of the present invention was obtained.

EXAMPLE 3

A pressure-sensitive adhesive layer was formed in the same manner as in Example 1 except that a plaster solution was obtained by adding 10 parts of biperiden hydrochloride, 40 parts of isopropyl myristate and 1.15 parts of sodium hydroxide, each relative to 48.85 parts of the solid content of the pressure-sensitive adhesive, to an ethyl acetate solution of an acrylic pressure-sensitive adhesive [a 75:3:22 (weight ratio) copolymer of 2-ethylhexyl acrylate, acrylic acid and vinyl pyrrolidone], adding to the resulting mixture 1.6 parts, relative to 100 parts of the solid content of the pressure-sensitive adhesive, of an isocyanate crosslinking agent, and then mixing the resulting mixture uniformly. The pressure-sensitive adhesive layer so formed was adhered to one side of a polyethylene film (thickness: 25 urm) serving as a backing material, whereby a percutaneous absorption preparation of the present invention was obtained.

EXAMPLE 4

To an ethyl acetate solution of an acrylic pressure-sensitive adhesive [a 95:5 (weight ratio) copolymer of 2-ethylhexyl acrylate and acrylic acid], 5 parts of biperiden and 40 parts of isopropyl myristate, each relative to 55 parts of the solid content of the pressure-sensitive adhesive, were added, followed by the addition of 0.15 part, relative to 100 parts of the solid content of the pressure-sensitive adhesive, of an isocyanate crosslinking agent. The resulting mixture was mixed uniformly to obtain a plaster solution. The resulting plaster solution was applied to one side of a polyester film serving as a separator to give a dry thickness of 40 $\mu$m and dried, whereby a pressure-sensitive adhesive layer was formed.

The pressure-sensitive adhesive layer so formed was adhered to one side of a polyester film (thickness: 12 $\mu$m) serving as a backing material, whereby a percutaneous absorption preparation of the present invention was obtained.

EXAMPLE 5

A pressure-sensitive adhesive layer was formed in the same manner as in Example 4 except that an ethyl acetate solution of an acrylic pressure-sensitive adhesive [a 75:3:22 (weight ratio) copolymer of 2-ethylhexyl acrylate, acrylic acid and vinyl pyrrolidone] was used and the isocyanate crosslinking agent was added in an amount of 0.4 part per 100 parts of the pressure-sensitive adhesive solid content.

The pressure-sensitive adhesive layer so formed was adhered to the surface of the nonwoven fabric side of a laminate made of a polyester film (thickness: 6 $\mu$m) and polyester nonwoven fabric (basis weight: 8 g/m$^-$) serving as a backing material, whereby a percutaneous absorption preparation of the present invention was obtained.

EXAMPLE 6

To a hexane solution of a rubber pressure-sensitive adhesive (polyisobutylene base), 10 parts of biperiden and 40 parts of isopropyl myristate, each relative to 50 parts of the solid content of the adhesive, were added and the resulting mixture was mixed uniformly, whereby a plaster solution was obtained. The resulting plaster solution was applied to one side of a polyester film serving as a separator to give a dry thickness of 40 $\mu$m and dried, whereby the pressure-sensitive adhesive layer was obtained.

The pressure-sensitive adhesive layer so formed was adhered to one side of a polyester film (thickness: 12 $\mu$m) serving as a backing material, whereby a percutaneous absorption preparation of the present invention was obtained.

EXAMPLE 7

To an ethyl acetate solution of an acrylic pressure-sensitive adhesive [a 95:5 (weight ratio) copolymer of 2-ethylhexyl acrylate and acrylic acid], 10 parts of trihexyphenidyl hydrochloride and 40 parts of isopropyl myristate, each relative to 50 parts of the solid content of the pressure-sensitive adhesive, were added, followed by the addition of 0.15 part, relative to 100 parts of the solid content of the pressure-sensitive adhesive, of an isocyanate crosslinking agent. The resulting mixture was mixed uniformly to obtain a plaster solution. The resulting plaster solution was applied to one side of a polyester film serving as a separator to give a dry thickness of 40 $\mu$m and dried, whereby a pressure-sensitive adhesive layer was formed.

The pressure-sensitive adhesive layer so formed was adhered to one side of an ethylene-vinyl acetate copolymer film (thickness: 25 $\mu$m) serving as a backing material, whereby a percutaneous absorption preparation of the present invention was obtained.

EXAMPLE 8

A pressure-sensitive adhesive layer was formed in the same manner as in Example 7 except that an ethyl acetate solution of an acrylic pressure-sensitive adhesive [a 75:3:22 (weight ratio) copolymer of 2-ethylhexyl acrylate, acrylic acid and vinyl pyrrolidone] was used and the isocyanate crosslinking agent was added in an amount of 0.4 part per 100 parts of the solid content of the pressure-sensitive adhesive.

The pressure-sensitive adhesive layer so formed was adhered to the nonwoven fabric side of a laminate made of a polyester film (thickness: 6 $\mu$m) and a polyester nonwoven fabric (basis weight: 8 g/m$^2$) serving as a backing material, whereby a percutaneous absorption preparation of the present invention was obtained.

EXAMPLE 9

A pressure-sensitive adhesive layer was formed in the same manner as in Example 7 except that 10 parts of trihexyphenidyl hydrochloride, 40 parts of isopropyl myristate and 1.15 parts of sodium hydroxide, each relative to 48.85 parts of the solid content of the pressure-sensitive adhesive, were added to an ethyl acetate solution of an acrylic pressure-sensitive adhesive [a 75:3:22 (weight ratio) copolymer of 2-ethylhexyl acrylate, acrylic acid and vinyl pyrrolidone], followed by the addition of 1.6 parts, relative to 100 parts of the solid content of the pressure-sensitive adhesive, of an isocyanate crosslinking agent.

The pressure-sensitive adhesive layer so formed was adhered to one side of a polyethylene film (thickness: 25 Pm) serving as a backing material, whereby a percutaneous absorption preparation of the present invention was obtained.

EXAMPLE 10

To an ethyl acetate solution of an acrylic pressure-sensitive adhesive [a 95:5 (weight ratio) copolymer of 2-ethylhexyl acrylate and acrylic acid], 5 parts of trihexyphenidyl and 40 parts of isopropyl myristate, each relative to 55 parts of the solid content of the pressure-sensitive adhesive, were added, followed by the addition of 0.15 part, relative to 100 parts of the solid content of the pressure-sensitive adhesive, of an isocyanate crosslinking agent. The resulting mixture was mixed uniformly to obtain a plaster solution. The resulting plaster solution was applied to one side of a polyester film serving as a separator to give a dry thickness of 40 µm and dried, whereby a pressure-sensitive adhesive layer was formed.

The pressure-sensitive adhesive layer so formed was adhered to one side of a polyester film (thickness: 12 µm) serving as a backing material, whereby a percutaneous absorption preparation of the present invention was obtained.

EXAMPLE 11

A pressure-sensitive adhesive layer was formed in the same manner as in Example 10 except that an ethyl acetate solution of an acrylic pressure-sensitive adhesive [a 75:3:22 (weight ratio) copolymer of 2-ethylhexyl acrylate, acrylic acid and vinyl pyrrolidone] was used and the isocyanate crosslinking agent was added in an amount of 0.4 part per 100 parts of the pressure-sensitive adhesive solid content.

The pressure-sensitive adhesive layer so formed was adhered to the nonwoven fabric side of a laminate made of a polyester film (thickness: 6 µm) and a polyester nonwoven fabric (basis weight: 8 g/m$^2$) serving as a backing material, whereby a percutaneous absorption preparation of the present invention was obtained.

EXAMPLE 12

To a hexane solution of a rubber pressure-sensitive adhesive (polyisobutylene base), 10 parts of trihexyphenidyl and 40 parts of isopropyl myristate, each relative to 50 parts of the solid content of the adhesive, were added and the resulting mixture was mixed uniformly, whereby a plaster solution was obtained. The resulting plaster solution was applied to one side of a polyester film serving as a separator to give a dry thickness of 40 µm and dried, whereby the pressure-sensitive adhesive layer was obtained.

The pressure-sensitive adhesive layer so formed was adhered to one side of a polyester film (thickness: 12 µm) serving as a backing material, whereby a percutaneous absorption preparation of the present invention was obtained.

Test 1

The percutaneous absorption preparation obtained in each of above Examples was punched out into a piece having a diameter of 6 mm. It was adhered to the central part of a cast skin of a snake having a diameter of 3 cm and set on a penetration testing apparatus. The skin penetration of biperiden toward water on the receptor side was measured. The penetration of biperiden hydrochloride or trihexyphenidyl hydrochloride was indicated in terms of biperiden or trihexyphenidyl. Results are shown in FIG. 1 (Examples 1 to 6) and FIG. 2 (Examples 6 to 12).

Figure 2:
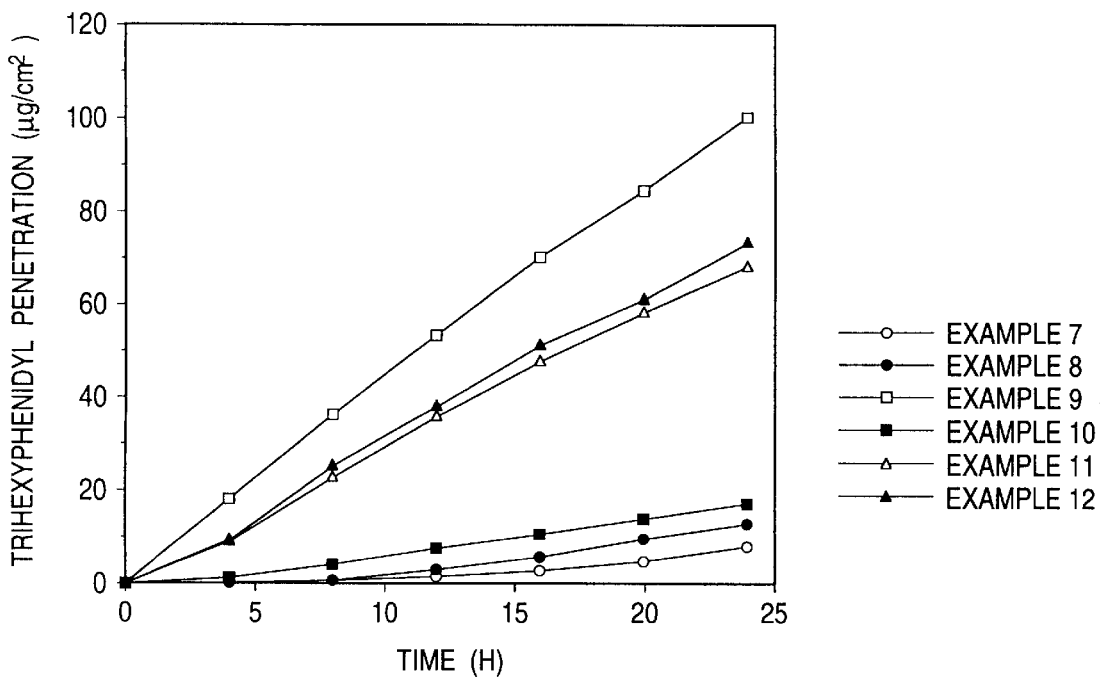
FIG. 2 is a graph illustrating the testing results of the preparations obtained in Examples 7 to 12.

As is apparent from FIGS. 1 and 2, it has been found that the percutaneous absorption preparation of the present invention is excellent in transcutaneous penetration of biperiden, trihexyphenidyl and hydrochlorides thereof, which suggests the possibility of percutaneous administration of them.

Test 2

The percutaneous absorption preparation obtained in each of the above Examples was punched out into a piece of 10 cm$^2$ and was stored for one month under the conditions of 25° C.×75% R.H., 40° C.×75% R.H. and 50° C., respectively. The ratio of the medicament content after storage to the medicament content before storage (the remaining ratio of the medicament) was measured and results are shown in Table 1 (Examples 1 to 6) and Table 2 (Examples 7 to 12).

TABLE 1

| | Medicament Remaining Ratio (%) | | |
|---|---|---|---|
| Example | 25° C., 75% R.H. | 40° C., 75% R.H. | 50° C. |
| 1 | 96.9 | 96.9 | 96.6 |
| 2 | 96.1 | 97.4 | 96.2 |
| 3 | 96.6 | 96.6 | 97.1 |
| 4 | 98.8 | 98.5 | 97.5 |
| 5 | 96.9 | 98.3 | 97.6 |
| 6 | 99.8 | 98.3 | 98.7 |

TABLE 2

| | Medicament Remaining Ratio (%) | | |
|---|---|---|---|
| Example | 25° C., 75% R.H. | 40° C., 75% R.H. | 50° C. |
| 7 | 98.5 | 98.3 | 98.3 |
| 8 | 97.5 | 98.1 | 96.0 |
| 9 | 99.5 | 99.5 | 99.1 |
| 10 | 98.7 | 99.0 | 98.5 |
| 11 | 98.9 | 100.3 | 97.9 |
| 12 | 99.3 | 99.5 | 98.9 |

As is apparent from the results of Tables 1 and 2, it has been found that any one of the percutaneous absorption preparations of the present invention retains the medicament stably.

While the invention has been described in detail and with reference to specific embodiments thereof, it will be apparent to one skilled in the art that various changes and modifications can be made therein without departing from the spirit and scope thereof.

What is claimed is:

1. A percutaneous absorption preparation which comprises a skin contact base containing biperiden-HCl in an amount of from 0.5 to 60% by weight, a freeing agent, and wherein the skin contact base is pressure sensitive adhesive having adhesion at room temperature and a layer made of said pressure-sensitive adhesive is formed on one side of a backing material, wherein said pressure sensitive adhesive is at least one of an acrylic pressure sensitive adhesive and a rubber pressure sensitive adhesive.

2. The percutaneous absorption preparation of claim 1, wherein said pressure-sensitive adhesive is an acrylic pressure-sensitive adhesive comprising alkyl acrylate or alkyl methacrylate.

3. The percutaneous absorption preparation of claim 1, wherein said skin contact base contains at least one organic liquid ingredient selected from the group consisting of glycols, oils and fats, fatty acids, alcohols and fatty acid esters.

4. The percutaneous absorption preparation of claim 3, wherein said skin contact base contains the at least one organic liquid ingredient in an amount of 2 to 50% by weight.

5. The percutaneous absorption preparation of claim 1 wherein the skin contact base contains biperiden-HCl in an amount of from 1% to 30% by weight.

6. The percutaneous absorption preparation of claim 1, wherein the freeing agent is selected from the group consisting of sodium hydroxide, potassium hydroxide, tetraethylamine, tetraethylammonium, amonia, and sodium caprylate.

7. The percutaneous absorption preparation of claim 6 wherein the freeing agent is sodium hydroxide.

8. The percutaneous absorption preparation of claim 7 wherein the sodium hydroxide is present in a ratio of 1.5 parts per 10 parts biperiden HCl.

* * * * *